US010342229B2

(12) United States Patent
Shirley et al.

(10) Patent No.: US 10,342,229 B2
(45) Date of Patent: Jul. 9, 2019

(54) AQUEOUS COATING COMPOSITIONS

(75) Inventors: Ian Malcolm Shirley, Bracknell (GB); Michael John Bean, Bracknell (GB); Catherine Julia Piper, Bracknell (GB); John Martin Silverthorne, Bracknell (GB); Ian David Tovey, Bracknell (GB); Patrick Joseph Mulqueen, Bracknell (GB)

(73) Assignee: Syngenta Participations AG, Basel (CH)

( * ) Notice: Subject to any disclaimer, the term of this patent is extended or adjusted under 35 U.S.C. 154(b) by 591 days.

(21) Appl. No.: 13/588,535

(22) Filed: Aug. 17, 2012

(65) Prior Publication Data

US 2012/0308631 A1 Dec. 6, 2012

Related U.S. Application Data

(63) Continuation of application No. 11/722,828, filed as application No. PCT/GB2005/005052 on Dec. 23, 2005, now abandoned.

(30) Foreign Application Priority Data

Dec. 30, 2004 (EP) ..................... 04258203

(51) Int. Cl.
*A01N 25/10* (2006.01)
*A01N 25/28* (2006.01)
*A01N 25/34* (2006.01)
*A01N 31/16* (2006.01)
*A01N 53/00* (2006.01)

(52) U.S. Cl.
CPC ............. *A01N 31/16* (2013.01); *A01N 25/10* (2013.01); *A01N 25/28* (2013.01); *A01N 25/34* (2013.01); *A01N 53/00* (2013.01)

(58) Field of Classification Search
None
See application file for complete search history.

(56) References Cited

U.S. PATENT DOCUMENTS

| 5,169,631 | A | * | 12/1992 | Rase et al. | 424/401 |
| 5,834,006 | A | * | 11/1998 | Smith et al. | 424/409 |
| 6,329,319 | B1 | * | 12/2001 | Puglisi et al. | 504/100 |
| 6,419,942 | B1 | * | 7/2002 | Lo et al. | 424/408 |
| 2001/0008874 | A1 | * | 7/2001 | Igari et al. | 504/359 |
| 2002/0081337 | A1 | * | 6/2002 | Kitagaki et al. | 424/497 |

FOREIGN PATENT DOCUMENTS

| DE | 2518507 | | 11/1975 | | |
| EP | 0238184 | * | 2/1987 | | |
| JP | 02209230 | | 8/1990 | | |
| JP | 05346047 | | 12/1993 | | |
| JP | 06219906 | | 8/1994 | | |
| JP | 06228469 | | 8/1994 | | |
| JP | 07010703 | | 1/1995 | | |
| JP | 07173005 | | 7/1995 | | |
| JP | 10059811 | * | 3/1996 | ............ | A01N 47/46 |
| JP | 10059811 | | 3/1998 | | |
| JP | 2004292317 | | 10/2004 | | |
| WO | 02062577 | | 8/2002 | | |

OTHER PUBLICATIONS

Levy et al. "Molecular basis of triclosan activity", Nature, 398, 1999, pp. 383-384.*

* cited by examiner

*Primary Examiner* — Melissa L Fisher
(74) *Attorney, Agent, or Firm* — James Cueva

(57) ABSTRACT

A pesticidal coating composition is provided which comprises an aqueous dispersion of at least one film-forming binder and at least one microencapsulated pesticide; wherein a coating prepared from such composition is substantially water-impermeable upon curing. The present invention further provides methods of coating substrates with the pesticidal coating composition, as well as substrates coated with the composition. The pesticidal coating compositions of the invention can be applied to substrates by professionals or non-professionals by spraying, painting, rolling, or brushing, before, during, or after construction.

10 Claims, No Drawings

US 10,342,229 B2

AQUEOUS COATING COMPOSITIONS

This application is a continuation of U.S. application Ser. No. 11/722,828, filed Jun. 26, 2007, which is a 371 of International Application No. PCT/GB2005/005052 filed Dec. 23, 2005, which claims priority to EP 04258203.1 filed Dec. 30, 2004, the contents of which are incorporated herein by reference.

FIELD OF THE INVENTION

The field of the invention relates to aqueous coating compositions, methods for application thereof and methods for using such compositions to protect substrates from pests and pest damage.

BACKGROUND

Termites invade houses in their search for cellulosic foodstuffs. The damage to US properties is put at about $1 billion per annum. Various methods have been used to protect buildings from being infested with termites, and many more methods used to rid the buildings of termites once infested.

The market has historically been dominated by pre-construction intensive spray application of long residual pesticides on to a foundation soil surface prior to the laying of the concrete slab over a plastic sheet such as a Damp-Proof Membrane-DPM, vapor barrier, vapor retarder or the like. Such pesticides as organo-phosphates-eg chlorpyrifos, pyrethroids eg cypermethrin have been employed. More recently, products such as imidacloprid and fipronil have been employed. Other, more environmentally acceptable, methods of termite-proofing a dwelling place have also been developed such as establishing physical barriers to termite entry (eg stainless steel mesh underlays, thick paints, composite materials). These have usually not contained pesticides.

Baiting is another method to control termites. Bait stations are installed underground around the perimeter of the house, for example, every 10 to 20 feet and 2 feet out from the house. This method takes considerable time to eliminate a colony of up to one year. It relies upon individual termites feeding on the bait, and returning to the colony to pass the poison on to other members, killing a portion of the exposed colony. However, termites that are not attracted to the bait may seek out wood in the building to feed on.

Other technologies include the use as a barrier of manufactured plastic films or composite film sheets that incorporate a termiticide. Drawbacks with this concept include long (and therefore costly) installation times and difficulty with sealing effectively what are termed "ground penetrations". These ground penetrations arise as a result of having to install piping (for water, heating, waste disposal) underground that rise up through the hardcore base of the building sub-structure and come into the building. Sealing these penetrations against termite entry is a key component of such systems and requires the careful installation of shaped polymer articles of the same composition. When carried out carefully by expert installation engineers, the whole barrier is extremely effective in preventing termite access to a house though the concrete sub-floor slab. However, unless sufficient care is taken, gaps or openings in joints would be inevitable, allowing for points of termite passage. This process is obviously time consuming and therefore expensive.

In many of these processes, the permeability to water of the formed film or coating and the release rate of the insecticide play decisive roles in the resistance and residual effectiveness of the barrier to wood-boring insect attack.

There exists a need for an easily installed pest resistant barrier that offers similar benefits of low environmental impact with long residual effectiveness against fungi, insects and representatives of the order acarina including termites, wood-boring ants, wood-boring insects and spiders.

SUMMARY OF THE INVENTION

The present invention provides a pesticidal coating composition comprising an aqueous dispersion of at least one film-forming binder and at least one microencapsulated pesticide; wherein a coating prepared from such composition is substantially water-impermeable upon curing. The inventive coating composition may also contain antimicrobial agents, non-encapsulated pesticides, or other additives such as rheology control agents, thickeners, surfactants, pigments, fillers, dispersants, freeze-thaw stabilizers and coalescents.

The present invention further provides methods of coating substrates with the pesticidal coating composition, as well as substrates coated with the composition. The pesticidal coating compositions of the invention can be applied to substrates by professionals or non-professionals by spraying, painting, rolling, or brushing, before, during, or after construction.

Definitions

In the ensuing detailed description, certain terms as well as certain terminology (generally known by those skilled in the art) will be utilized for purposes of conciseness, and for otherwise elucidating the features and advantages of the present invention. Such terms are either defined as follows or are otherwise intended to mean the following.

The term "aqueous" in the context of the present invention is understood to denote water or, optionally, a water-based solvent system or carrier comprising a mixture of water and a water-miscible organic solvent such as a solvent selected from the ketones, esters, ethers, cyclic amides or sulfoxides. Particular examples of these solvents include acetone, ethyl alcohol, methyl alcohol, isopropyl alcohol, dimethylformamide, methyl-ethyl ketone, butyl lactate, N-methylpyrrolidone, ethylene glycol and propylene glycol ethers such as 2-butoxyethanol, 2-(2-butoxyethoxy)ethanol, and the like. A mixture of water with two or more water-miscible organic solvents such as those cited above may be used. In one embodiment, a water-based solvent system comprises a mixture of a major amount of water with a minor amount of such a water-miscible organic solvent or solvent mixture. In another embodiment, aqueous denotes at least 60% water; or at least 70% water; or at least 80% water; or at least 90% water; or at least 95% water; or water which is substantially free of organic solvents The term "ambient temperature" shall be understood to mean a temperature of from about 0 degrees Celsius to about 50 degrees Celsius; or particularly from about 15 degrees Celsius to about 32 degrees Celsius; or more particularly from about 20 degrees Celsius to about 25 degrees Celsius.

The term "dispersion" is understood to connote a multi-phase system wherein at least one phase consists of finely-divided particles, often in the colloidal-size range, distributed throughout a "bulk" substance or carrier, wherein such finely-divided particles provide the "disperse" or internal phase and the bulk substance provides the "continuous" or external phase.

The term "latex" as used herein is intended to mean (i) any polymeric product produced as an aqueous suspension emulsion polymerization process and includes within its scope both synthetic latexes and natural latexes; and (ii) post-dispersed suspensions such polyurethane dispersions and silicone dispersions.

The term "emulsion" is understood by those skilled in the art as involving a stable mixture of two or more immiscible liquids held in suspension by small percentages of substances called "emulsifiers" (also called "surfactants" or "soaps"). All emulsions are known to include both a continuous phase as well as a discontinuous phase that is dispersed throughout the continuous phase.

The term "emulsion polymerization" is understood by those skilled in the art as involving the polymerization of monomers in aqueous media to form dispersed polymers having particle diameters in the range of approximately 20 to 1000 nanometers.

The term "glass-transition temperature" or "Tg" is understood by those skilled in the polymer chemistry art as representing the temperature at which the amorphous domains of a polymer take on the characteristic properties of the "glassy" state, wherein such polymeric glassy-state properties include brittleness, stiffness and rigidity.

The term "microencapsulated pesticide" is understood to refer to small solid particles or liquid droplets of a compound (other than an insecticidal organophosphorus compound) which has a lethal effect on pests such as insects, fungi or arachnids of a type to be controlled (namely that the application of an appropriate amount of such compound results in death of a substantial portion of the pests being treated) coated with a thin film of a polymer coating or shell material. In general, the term microencapsulated pesticide (including microencapsulated insecticide, microencapsulated fungicide or microencapsulated acaricide) is used to describe particles with diameters between 0.1 and 1000 µm.

The term "pesticide product" refers to the combination of active and inert constituents associated with a microencapsulated pesticide that is used alone or in combination with one or more non-encapsulated pesticides.

The term "Minimum film-forming temperature" or "MFFT" means the minimum temperature at which the formulated composition containing a water-borne synthetic latex or emulsion will coalesce when laid on a substrate as a thin film.

The term "substantially water-impermeable" as used herein in reference to coatings of the invention, refers to material that is sufficiently impermeable to water, such that there is substantially no migration of water into or out of the coating as confirmed by ASTM D 870-02 at 20 degrees Celsius.

A number of additional terms are defined further below, throughout the body of this patent specification.

DESCRIPTION OF SPECIFIC EMBODIMENTS

While the present invention is susceptible to several embodiments in various forms, there is hereinbelow described in detail certain specific embodiments, with the understanding that the present disclosure is to be considered as merely an exemplification of the present invention, without limitation to the specific embodiments or examples discussed.

In accordance with one aspect of the present invention, it has been discovered that coatings having improved resistance to wood pests such as termites can be obtained from an aqueous insecticidal composition comprising a dispersion of at least one water-insoluble, film-forming polymeric binder and at least one microencapsulated insecticide; wherein coatings prepared from such compositions are substantially water-impermeable.

In accordance another aspect of the present invention, it has been discovered that both the water resistance of barrier coatings, the release rate and stability of pesticides from coated substrates can be better controlled by applying an aqueous pesticidal composition comprising a latex dispersion containing at least one microencapsulated pesticide to a target substrate, and then curing the latex to form a substantially water-impermeable polymer coating containing a microencapsulated pesticide on the surface of the substrate.

Accordingly, in one embodiment, the present invention provides a pesticidal coating composition comprising a dispersion of at least one water-insoluble, film-forming polymeric binder and at least one microencapsulated pesticide in an aqueous carrier; wherein coatings prepared from such composition are substantially water-impermeable upon curing.

The film-forming portion of the present pesticidal aqueous coating composition, comprising polymeric components, is referred to as the "binder" and is dispersed in the aqueous carrier. The binder generally includes all the normally solid polymeric, non-liquid components of the composition. Generally, microcapsules, pigments, pesticides, chemical additives such as stabilizers or dispersing aids and fillers are not considered part of the binder.

The binder can be present in any amount, but the concentration of the binder in the composition that is used to form the cured film or coating should be low enough to permit easy handling and application of the aqueous coating composition to the target substrate—such as by spraying—and thorough distribution of the film so that the target substrate is substantially covered. However, the concentration should be high enough, when used in combination with the other parameters of coating technology, to avoid the loss of polymer from the substrate by dripping or pooling of the composition and to provide a coherent, robust film on drydown.

In one embodiment, a film-forming effective amount of binder in the composition is sufficient to provide a cured coating which comprises at least about 50% by weight of the binder; in particular at least about 60% by weight; more particularly at least about 75% by weight, and most particularly at least about 80% by weight of the final cured coating.

In one embodiment, the ratio of polymer to pesticidal product in the dry coating at the time that a film of the composition cures is at least 70:30 polymer:pesticide product, particularly 80:20 polymer:pesticide product and more particularly 85:15 polymer:pesticide product.

In one embodiment, a non-binder solid such as fiber is added to improve cohesion and flow characteristics of the coating composition. Among the suitable fibers there may be mentioned glass fibers. The fibers help to prevent the liquid surface coating from sagging on pitched or vertical surfaces of target substrates during drying and to improve robustness and structural integrity of the dry film.

Other non-binder solids include fillers such as clay, calcium carbonate, and titanium dioxide Polymers that can be used as a binder are those that are capable of forming a substantially water-impermeable coating upon curing.

When it is said that the coating is substantially water-impermeable, it is best tested by an appropriate water resistance test (for example, ASTM Method D 870-2). Among the advantages that a coating having low water permeability provides is that the loss of the pesticide due to water solubilization dispersion in the environment is reduced. It is also advantageous if the binder polymer is one that is compatible with the polymer in the wall of the microcapsule employed in the composition.

In one embodiment, the binder is a latex which coalesces or cures to a coating that is substantially impermeable to water. The binder is selected so that the coating that is formed from the aqueous coating composition has a resultant MFFT or film formation temperature of the cured composition within a pre-selected range, thereby providing a coating which is substantially water-impermeable and retards the release rate of the pesticide from the coating by a desired amount. The MFFT range would be the likely ambient temperatures achieved across the range of application techniques for such products. In one embodiment, this would be 0-50° C. In another embodiment, the MFFT of the composition is from about 15 to about 32° C. This film formation temperature can be adjusted not only by selection of the polymer type (through Tg, etc) but also by other components in the composition such as surfactants, coalescing agents, and the like.

The latex dispersion employed in the inventive aqueous coating compositions is derived from a wide variety of polymers and co-polymers and combinations thereof. Suitable latexes for use in the composition comprise polymers and copolymers of styrene, alkyl styrenes, isoprene, butadiene, acrylonitrile lower alkyl acrylates, vinyl chloride, vinylidene chloride, vinyl esters of lower carboxylic acids and alpha, beta-ethylenically unsaturated carboxylic acids, including polymers containing three or more different monomer species copolymerized therein, as well as post-dispersed suspensions of silicones or polyurethanes.

In one embodiment, the size of the polymeric particles in the dispersion are in the range of from 0.03 to 20 microns; more particularly from 0.1 to 10 microns. The present invention also contemplates latex dispersions having bi-modal or multi-modal particle size distributions.

In another aspect of the invention, small amounts, for example from 0 to 10 percent by weight of the binder of multifunctional monomers may be employed to crosslink the latex polymers, if desired, to improve water resistance and pesticidal release characteristics. In one embodiment, the multifunctional monomer is bifunctional.

If it is desirable, the latex binders described herein can be compounded with, or have mixed therein, other known ingredients such as plasticizers, emulsifiers, stabilizers, curing agents, fillers, antioxidants, antifoaming agents, dying adjuvants, levelling agents, pigments, or other compounding aids. Furthermore, thickeners or bodying agents may be added to the polymer latexes so as to control the viscosity of the latexes and thereby achieve the proper flow properties for the particular application desired. Such materials are well known in the art.

The non-film-forming ingredients of the coating composition and cured coating herein further comprise at least one pesticide product comprising at least one microencapsulated pesticide and, optionally, one or more non-microencapsulated pesticides. The microencapsulated pesticide portion of the pesticide product is present in an amount of at least 1% by weight of the cured coating. The amount of any non-microencapsulated pesticides that are present in the composition are utilized in an amount of from 0 to about 99% by weight of the entire pesticide product present in the cured composition.

In one embodiment, the pesticide products in the aqueous composition and cured film coating including insecticides, acaricides and fungicides are employed at rates dependent on their activity levels for the desired end use. For example, in one embodiment, suitable rates for the pesticide products are the existing rates given on the current product labels for such pesticide products.

Microencapsulated pesticide active ingredients suitable for use in the coating compositions and cured coatings according to the invention are prepared with any suitable technique known in the art. For example, various processes for microencapsulating material have been previously developed. These processes can be divided into three categories—physical methods, phase separation and interfacial reaction. In the physical methods category, microcapsule wall material and core particles are physically brought together and the wall material flows around the core particle to form the microcapsule. In the phase separation category, microcapsules are formed by emulsifying or dispersing the core material in an immiscible continuous phase in which the wall material is dissolved and caused to physically separate from the continuous phase, such as by coacervation, and deposit around the core particles. In the interfacial reaction category, microcapsules are formed by emulsifying or dispersing the core material in an immiscible continuous phase and then an interfacial polymerization reaction is caused to take place at the surface of the core particles. The concentration of the pesticidal active ingredient present in the microcapsules can vary from 0.1 to 60% by weight of the microcapsule.

In one aspect, suitable microcapsule wall materials are selected from the polyureas, aminoplasts, polyurethanes and polyamides.

In one embodiment, polyurea microcapsules containing a suitable termiticide are prepared as exemplified in U.S. Pat. No. 4,285,720, which involves the use of at least one polyisocyanate such as polymethylene polyphenylisocyanate (PMPPI) and/or tolylene diisocyanate (TDI) as the prepolymer. In the creation of polyurea microcapsules, the wall-forming reaction is initiated by heating the emulsion to an elevated temperature at which point the isocyanate polymers are hydrolyzed at the interface to form amines, which in turn react with unhydrolyzed polymers to form the polyurea microcapsule wall.

Examples of suitable insecticidal, termiticidal or acaricidal active ingredients for use in the aqueous coating composition and cured coatings include, but are not limited to, pyrethrins and synthetic pyrethroids; bisamides, oxadizine derivatives; chloronicotinyls; nitroguanidine derivatives; organophosphates; pyrrols; pyrazoles; phenyl pyrazoles; diacylhydrazines; biological/fermentation products; carbamates and combinations of these types of compounds.

In one aspect, suitable insecticides, termiticides or acaricides for use in the inventive aqueous compositions and cured coatings include tefluthrin, permethrin, lambda cyhalothrin, resmethrin, deltamethrin, cypermethrin, cyphenothrin, cyfluthrin, deltamethrin, chlorpyrifos, fenoxycarb, diazinon, dichlorophen, methyl isothiocyanate, pentachlorophenol, tralomethrin, chlorfenapyr, fipronil, neonicotinoids and combinations of these compounds. Examples of suitable neonicotinoids include, but are not limited to, thiamethoxam, nitenpyram, imidacloprid, clothianidin, acetamiprid, and thiacloprid. Insecticidal organophosphorus compounds such as pirimiphos-methyl, primiphos-ethyl, chorpyrifos, diazinon and the like are not included among the microencapsulated pesticides suitable for use in accordance with the present invention.

One specific class of pesticides for use in the microcapsules are the class of cyhalothrins including lambda cyhalothrin and gamma cyhalothrin. As noted above, in one embodiment, suitable rates for the pesticide are the existing rates given on the current product labels for pesticide products containing such pesticide.

Examples of fungicidal compounds which may be included in the composition of the invention are AC 382042 (N-(1-cyano-1,2-dimethylpropyl)-2-(2,4-dichlorophenoxy) propionamide), acibenzolar-5-methyl, alanycarb, aldimorph, anilazine, azaconazole, azafenidin, azoxystrobin, benalaxyl, benomyl, benthiavalicarb, biloxazol, bitertanol, blasticidin S, boscalid (new name for nicobifen), bromuconazole, Bronopol, bupirimate, captafol, captan, carbendazim, carbendazim chlorhydrate, carboxin, carpropamid, carvone, CGA 41396, CGA 41397, chinomethionate, chlorbenzthiazone, chlorothalonil, chlorozolinate, clozylacon, copper containing compounds such as copper oxychloride, copper oxyquinolate, copper sulphate, copper tallate, and Bordeaux mixture, cyamidazosulfamid, cyazofamid (IKF-916), cyflufenamid, cymoxanil, cyproconazole, cyprodinil, debacarb, di-2-pyridyl disulphide 1,1'-dioxide, dichlofluanid, diclocymet, diclomezine, dicloran, diethofencarb, difenoconazole, difenzoquat, diflumetorim, diiodomethyl-p-tolyl-sulfone (Amical, from Dow) O,O-di-iso-propyl-5-benzyl thiophosphate, dimefluazole, dimetconazole, dimethirimol, dimethomorph, diniconazole, dinocap, dithianon, Dithiocarbamates, dodecyl dimethyl ammonium chloride, dodemorph, dodine, doguadine, edifenphos, epoxiconazole, ethaboxam, ethirimol, ethyl (Z)—N-benzyl-N([methyl(methylthioethylideneaminooxycarbonyl)amino]thio)-β-alaninate, etridiazole, famoxadone, fenamidone, fenarimol, fenbuconazole, fenfuram, fenhexamid, fenoxanil (AC 382042), fenpropidin, fenpropimorph, fentin acetate, fentin hydroxide, ferbam, ferimzone, fluazinam, fludioxonil, flumetover, flumorph, fluoroimide, fluquinconazole, flusilazole, flusulfamide, flutolanil, flutriafol, folpet, fosetyl-aluminium, fuberidazole, furalaxyl, furametpyr, guazatine, hexaconazole, hydroxyisoxazole, hymexazole, imazalil, imibenconazole, iminoctadine, iminoctadine triacetate, 3-iodo-2-propynyl butylcarbamate (IBPC), ipconazole, iprobenfos, iprodione, iprovalicarb, isopropanyl butyl carbamate, isoprothiolane, kasugamycin, kresoxim-methyl, LY186054, LY211795, LY 248908, mancozeb, maneb, MBT mefenoxam, mepanipyrim, mepronil, metalaxyl, metalaxyl M, metconazole, metiram, metiram-zinc, metrafenone, MON65500 (N-allyl-4,5-dimethyl-2-trimethylsilylthiophene-3-carboxamide), myclobutanil, NTN0301, neoasozin, nickel dimethyldithiocarbamate, nitrothale-isopropyl, nuarimol, 2-0-octyl-4-isothiazolin-3-one (Skane M 8 Rohm & Hass), ofurace, organomercury compounds, oxadixyl, oxasulfuron, oxolinic acid, oxpoconazole, oxycarboxin, pefurazoate, penconazole, pencycuron, phenazin oxide, phosphorus acids, phthalide, picoxystrobin, polyoxin D, polyram, probenazole, prochloraz, procymidone, propamocarb, propamocarb hydrochloride, propiconazole, propineb, propionic acid, proquinazid, prothioconazole, pyrazophos, Sodium and Zinc Pyrithione (Omadine chemistry from Arch Chem.), pyrifenox, pyrimethanil, pyroquilon, pyroxyfur, pyrrolnitrin, quaternary ammonium compounds, quinomethionate, quinoxyfen, quintozene, silthiofam (MON 65500), S-imazalil, simeconazole, sipconazole, sodium pentachlorophenate, spiroxamine, streptomycin, sulphur, tebuconazole, tecloftalam, tecnazene, tetraconazole, thifluzamide, 2-(thiocyanomethylthio)benzothiazole, thiophanate-methyl, thiram, tiadinil, timibenconazole, tolclofos-methyl, tolylfluanid, triadimefon, triadimenol, triazbutil, triazoxide, tricyclazole, tridemorph, triflumizole, triforine, triticonazole, validamycin A, vapam, vinclozolin, XRD-563, zineb, ziram, zoxamide and compounds of the formulae:

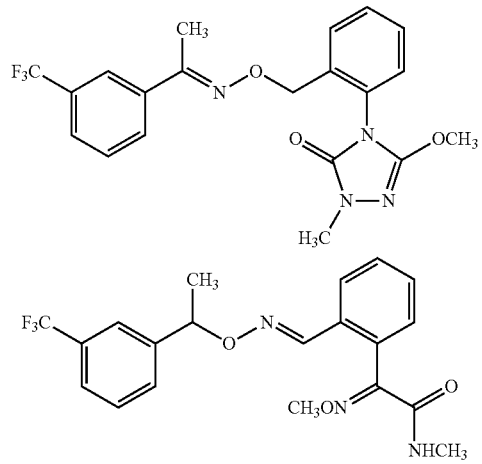

Examples of particularly suitable fungicides for use in the aqueous coating composition and cured coatings include, but are not limited to, the azoles such as cyproconazole, propiconazole, tebuconazole and difenoconazole; the strobilurins such as azoxystrobin, dimoxystrobin, fluoxastrobin, kresoxim-methyl, metominostrobin, orysastrobin, picoxystrobin, pyraclostrobin and trifloxystrobin; chlorothalonil; and thiabendazole. As noted above, in one embodiment, suitable rates for the fungicide are the existing rates given on the current product labels for pesticide products containing such fungicide.

Bacterial and other microbial problems arise from for example, from, *Escherichia coli, Samonella (typhimurum), Campylobacter. Listeria, Pseudomonas, Klebsiella.* Examples of suitable antimicrobial and/or antibacterial agents for use in the aqueous coating composition and cured coatings include, but at not limited to, triclosan and trichlocarbam. Such antibacterial agents may be added to the latex polymer composition either as a dispersion of technical material, suitably ground technical material or formulated in such a manner that the agent is imbibed into the polymer latex and thus distributed throughout the curing film.

In one embodiment, microencapsulated insecticides (optionally including at least one non-microencapsulated pesticide such as an insecticide or fungicide) are present in the coating composition in an amount to provide an effective barrier to insect pests such as arthropods which contact or come into the vicinity of coatings prepared from the compositions. As one skilled in the art can appreciate the exact amount will vary depending factors including the type of microcapsule employed, the substrate to be coated as well as the thickness and orientation (horizontal or vertical) of the coating. The insecticide of the coating must not prematurely dissipate and should be efficacious during that time in the target insects life cycle which may cause potential damage to wood portions of a building or other construction. One skilled in the art will appreciate that this time will vary depending on the target insect among other factors. In general the coating will be efficacious for at least one year for a surface treatment and at least 5 years for an under slab (concrete) treatment after curing. The barrier coating of the present invention will contain an amount of insecticide that is insecticidally effective. An insecticidally effective amount a used herein means that amount of insecticide that will kill insect pests or will consistently reduce or retard the amount of damage produced by insect pests.

In one aspect, target pests include insects and representatives of the order acarina such as termites, ants (such as carpenter ants) and spiders. More specifically, termites that may be controlled by the composition and method of the invention include, for example, *Reticulitermes* spp. such as *R. flavipes, R. hesperus, R. tibialis, R. virginicus, R. santonensis* and *R. hageni* and *Coptotermes* spp. such as *C. formosanus*.

Examples of target fungi are: *Alternaria alternata, Alternaria tenuissima, Aureobasidium pullulans, Aspergillus flavus, Aspergillus niger, Aspergillus terreus, Aspergillus fumigatus, Aspergillus repens, Aspergillus versicolor, Candida albicans, Cladosporium cladosporioides, Cladosporium herbarum, Cladosporium sphaerospermum, Coniophora puteana, Curvularia genticulata, Diplodia natalensis, Epidermophyton floccosum, Fusarium oxysporum, Gliocladium vixens, Gloeophyllum trabeum Humicola grisea, Lecythophora mutabilis, Lentinus cyathiformis, Lentinus lepidus, Memnionella echinata, Mucor indicus, Mucor racemosus, Oligoporus placenta, Paecilomyces variotii, Penicillium citrinum, Penicillium funiculosum, Penicillium ochrochloron, Penicillium purpurogenum, Penicillium pinophilum, Penicillium variabile, Petriella setifera, Phanerochaete chrysosporium, Phoma violacea, Poria placenta, Rhodotorula rubra, Schizophyllum commune, Sclerophoma phytiophila Scopulariopsis brevicaulis, Serpula lacrymans, Sporobolomyces roseus, Stachybotrys atra, Stachybotrys chartarum, Stemphylium dendriticum, Trichophyton mentagrophytes, Trichurus spiralis, Trichophyton rubrum, Ulocladium atrum* and *Ulocladium chartarum*. Of particular concern are: *Alternaria alternata, Alternaria tenuissima, Aspergillus niger, Aspergillus versicolor, Aureobasidium pullulans, Cladosporium cladosporioides, Coniophora puteana, Gloeophyllum trabeum, Memnionella echinata, Mucor indicus, Oligoporus placenta, Penicillium citrinum, Penicillium funiculosum, Penicillium pinophilum, Sclerophoma phytiophila, Stachybotrys atra, Stachybotrys chartarum*, and *Ulocladium chartarum*.

The application methods, such as spraying, misting, atomising, broadcasting, brushing, caulking, spreading, dipping or pouring, and the nature of the composition are adapted to suit the intended aims and the prevailing circumstances. Optimum rates of application of the inventive composition, for a particular target substrates and set of insect pressure conditions, can be determined easily and without undue experimentation by simple ranging studies carried out in wood such as in wooden building construction and wood which is in contact with soil for example fence posts, utility poles, railroad cross-ties and wooden supports, that can be structurally degraded by the action of one or more fungal or wood pests including, but not limited to, wood destructive fungi, termites, ants and other boring insects.

In one embodiment, the compositions of the invention are applied to substrates such as clean, dry surfaces, typically a concrete, cement or plastic surface such as a DPM (Damp-proof membrane), vapor or moisture barriers or retarders and in or around structures, such as, homes, buildings, utility penetrations, and wooden structures. DPM's can be a simple polyethylene membrane, a chemically etched polyethylene (such as Corona treated polyethylene for greater wetting, substantivity of the polymer film to the polyethylene sheet) or re-inforced, structured multilayer polyethylene sheets such as the product range sold under the Tradename GRIF-FOLYN® sold by Reef Industries, Inc. (Houston, Tex.). In one embodiment, films are formed on a target substrate. For some target substrates, e.g. around bathtraps, the thickness can be greater, indeed it can be employed to coat and substantially fill the void space.

After the film of coating composition has been applied to the target substrate, it is cured to form the polymer coating. When it is said that the film or coating is "cured", or when "curing" the film or coating is referred to, what is meant is that a solid coating of the binder is formed from the binder in the aqueous composition. Curing is often the result of drying of the liquid from the aqueous composition, and can also be achieved by coalescence, chemical reaction, adsorption, sequestration, or other forms of polymer curing that are known in the art. Chemical reaction can include cross linking of the drying film by incorporation of a suitable cross linking monomer into the polymer system. Cross linking monomers contain at least two polymerisable groups eg vinylic groups. Suitable monomers can include 1,4-butanediol diacrylate, 1,6-hexanediol diacrylate, 1,14-tetradecyldiol diacrylate, divinylbenzene, vinyl crotonate, divinyl ether, 1,3,5-triallyltriazine trione, ethylene glycol diacrylate, ethylene glycol dimethacrylate and mixtures thereof. Other reactivity can be induced by incorporation of labile chemistry that is induced by the drying process. External cross-linkers, when used, are generally compounds containing charged groups which interact with charged groups in the polymer. Suitable cross-linkers contain metal (eg Mg, Ca, Mn or Zn) cations or bidentateor multidentate amine groups. Other external cross-linkers are non-metallic and organic compounds eg triethylene tetramine, ethylene diamine, diethylaminopropylamine and bis(quaternary ammonium) salts. Some external cross-linkers do not have any effect until the coating is prepared, for example, a cation can be present as an ammonia complex and not become effective until the ammonia is removed during the drying step. Thus, an aqueous solution containing $Zn(NH_3)^{2+}$ ions can be employed in this manner. External Cross linking can be employed in combination with cross-linking monomers The barrier coating composition when coated onto substrates exhibits resistance to termite feeding such that if termites do attempt to feed on the coating, they find it not palatable or causes mortality. The main component used in the coating composition that either causes mortality or makes it not palatable is a microencapsulated pesticide. However, it is believed that the cured physical barrier coating also contributes synergistically to this protection against insects such as arthropods including termites and wood-boring ants by inhibition of feeding.

The following examples describe specific embodiments within the scope of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples. In the examples all percentages are given on a weight basis unless otherwise indicated.

EXAMPLES

Example 1—a Sprayable Coating is Prepared in the-Following Way

Neopac E106 (an aromatic polyurethane-acrylic copolymer, 889 g), and Scimitar® GC (also known as Demand® 10 CS) (a 9.7% lambda cyhalothrin Capsule Suspension (CS) formulation, 100.6 g) (Syngenta) were mixed together to form a homogeneous dispersion at room temperature using an overhead paddle stirrer mixer. Acrysol RM-8W, an associative thickener (12.7 g) was added to the dispersion and the composition was rolled at room temperature for 24 hours to ensure full dispersion and thickening.

Example 2

The procedure of Example 1 is repeated except that Neopac E106 is replaced with POLIDENE 33-004 (an aqueous emulsion of a vinylidene chloride copolymer containing a high VdC content available from Scott Bader Company 1080.3 g) and thickened with Tafigel PUR 41 (a PU rheology modifier, 9.90 g).

Example 3

The procedure of Example 1 is repeated except that Neopac E106 is replaced with Neocryl A-1049 (an anionically stabilised acrylic copolymer, 194.5 g), 2-butoxyethanol (a coalescent, 19.45 g) and Scimitar GC (7.94 g) were mixed together using an overhead paddle stirrer. Optiflow H370 (a non-ionic associative thickener, 3.9 g) was added to this homogeneous dispersion and paddle stirring continued for a further hour until the composition was fully thickened.

Example 4—Microencapsulated Lambda Cyhalothrin is Prepared as Follows

High Cross-Linked Capsule

A 55% w/w solution of lambda-cyhalothrin in Solvesso 100 (aromatic solvent, ex Exxon) was made by adding 5.69 g of molten lambda-cyhalothrin technical material (85% w/w lambda-cyhalothrin) to 3.13 g of Solvesso 100. To this was added 1.03 g of Polyalkylene polyphenolisocyanate "PAPI" (Suprasec 5025, ex Huntsman) and 0.34 g of toluene diisocyanate "TDI" technical material (80% w/w, ex Aldrich). This mixture is known as the oil phase.

An aqueous phase is prepared comprising 0.49 g of Celvol 205 (88% hydrolysed polyvinylalcohol, ex Celanese Chemicals) dispersed via high shear mixing into 29.71 g of deionised water. To this was added 0.25 g of Synperonic A7 (C13/15 alcohol ethoxylate, 7 moles ethoxylation, ex Uniqema) whilst mixing. Continuing to mix, the oil phase is slowly added to the emulsion phase and mixing speed adjusted to give a median particle size between 5 μm and 20 μm.

The temperature of the reaction vessel was then raised to 60° C. so as to initiate the wall formation reaction, and the temperature maintained, together with low shear mixing, for a period of 3 hours. 0.4 g of 35% ammonia solution (ex Aldrich) was then added to quench any unreacted isocyanate and the mixture allowed to stir for a further 30 minutes. The mixture was allowed to cool to room temperature prior to adjustment to pH 7 using 1 M sulphuric acid.

Aminoplast Capsule

A 55% w/w solution of lambda-cyhalothrin in Solvesso 100 (aromatic solvent, ex Exxon) was made by adding 11.70 g of molten lambda-cyhalothrin technical material (85% w/w lambda-cyhalothrin) to 6.54 g of Solvesso 100. To this was added 2.32 g of a butylated ureaformaldehyde resin (Cymel U-80, ex Cytec) and 0.34 g of Pentaerythritol tetrakis(3-mercaptopropionate) (Q43, ex Aldrich). This mixture is known as the oil phase.

An aqueous phase was prepared comprising 1.00 g of PVA (Gohsenol GL05) and 0.05 g sodium alkylnaphthalenesulfonate (Petro Baf, ex pilot chemicals) dissolved in 18.82 g of deionised water. The oil phase was slowly added to the emulsion phase and mixing speed adjusted to give a median particle size between 5 μm and 20 μm. The pH was then adjusted to pH2 with the addition of sulfuric acid and the temperature raised to 50° C. for 3 hours with continuous stirring. After cooling the pH was adjusted to ph5.5 with sodium hydroxide

Examples 5-34—Pesticidal Latex Coatings are Prepared in the Following Way

The following samples were prepared by adding the prescribed amounts of microencapsulated insecticide (or other product as defined) to a suitable latex polymer and (where applicable) the coalescent and appropriate inerts. The mixture was then thoroughly shaken and left to roll for an hour and visually assessed for physical compatibility. A small portion of each mixture was then smeared onto a glass slide and left to dry in order to produce a dried film with a common concentration of insecticide such as lambda-cyhalothrin. The quality of film formation and film quality of the dried films were assessed after 3 days. Each film was assessed to be a good film, non-tacky, and strongly adhered to the substrate.

The following materials are used in the examples which follow:

| Latex | Chemical Description | Latex supplier |
|---|---|---|
| Permax 803 | Vinylidene chloride acrylic copolymer | Noveon |
| Vinamul 3650 | Vinyl acetate-vinyl chloride-ethylene-acrylate | Vinamul Ltd |
| Haloflex 202 | Vinyl acrylic copolymer | Neoresins |
| Vinacryl 40224 | Acrylic latex, surfactant stabilised | Vinamul Ltd |
| Neocryl A-1049 | Modified acrylic styrene copolymer, anionic | Neoresins |
| Neopac E106 | Aromatic urethane acrylic, anionic | Neoresins |

TABLE 1

| Microencapsulated Pesticide | Solids Content | Lambda* Content | Wet Composition Ex #5 | | Dry Composition Ex #5 | | Wet Composition Ex #6 | | Dry Composition Ex #6 | | Wet Composition Ex #7 | | Dry Composition Ex #7 | |
|---|---|---|---|---|---|---|---|---|---|---|---|---|---|---|
| Scimitar/Demand 10CS Latexes | 32.50% | 9.68% | 0.16 g | 4.7% | 0.05 g | 2.6% | 0.16 g | 4.1% | 0.05 g | 2.6% | 0.16 g | 4.7% | 0.05 g | 2.6% |
| Permax 803 | 60% | | 3.25 g | 95.3% | 1.95 g | 97.4% | | | | | | | | |
| Vinamul 3650 | 52% | | | | | | 3.75 g | 95.9% | 1.95 g | 97.4% | | | | |
| Haloflex 202. Coalescent 2-butoxy-ethanol | 60% | | | | | | | | | | 3.25 g | 95.3% | 1.95 g | 97.4% |
| Lambda-Cyhalothrin* Content | | | 3.4 g | 100.0% | 2.0 g 0.015 g | 100.0% 0.77% | 3.9 g | 100.0% | 2.0 g 0.015 g | 100.0% 0.77% | 3.4 g | 100.0% | 2.0 g 0.015 g | 100.0% 0.77% |
| | | | Batch Size = 2.00 G | | | | Batch Size = 2.00 g | | | | Batch Size = 2.00 g | | | |
| | | | Ex #8 | | | | Ex #9 | | | | Ex #10 | | | |
| Scimitar/Demand 10CS Latexes | 32.50% | 9.68% | 0.16 g | 3.2% | 0.05 g | 2.6% | 0.16 g | 3.6% | 0.05 g | 2.6% | 0.16 g | 2.6% | 0.05 g | 2.6% |
| Vinacryl 40224 | 40% | | 4.87 g | 96.8% | 1.95 g | 97.4% | | | | | | | | |
| Neocryl A-1049 | 40% | | | | | | 3.90 g | 87.6% | 1.56 g | 77.9% | | | | |
| Neopac E106 Coalescent 2-butoxy-ethanol | 33% | | | | | | | | | | 5.90 g | 97.4% | 1.95 g | 97.4% |
| Lambda-Cyhalothrin* Content | | | 5.0 g | 100.0% | 2.0 g 0.015 g | 100.0% 0.77% | 4.4 g | 100.0% | 2.0 g 0.015 g | 100.0% 0.77% | 6.1 g | 100.0% | 2.0 g 0.015 g | 100.0% 0.77% |
| | | | Batch Size = 2.00 G | | | | Batch Size = 2.00 g | | | | Batch Size = 2.00 g | | | |

TABLE 2

| Microencapsulated Pesticide | Solids Content | Lambda* Content | Wet Composition Ex #11 | | Dry Composition Ex #11 | | Wet Composition Ex #12 | | Dry Composition Ex #12 | | Wet Composition Ex #13 | | Dry Composition Ex #13 | |
|---|---|---|---|---|---|---|---|---|---|---|---|---|---|---|
| Aminoplast CS Latexes | 44.36% | 20.00% | 0.08 g | 2.3% | 0.03 g | 1.7% | 0.08 g | 2.0% | 0.03 g | 1.7% | 0.08 g | 2.3% | 0.03 g | 1.7% |
| Permax 803 | 60% | | 3.33 g | 97.7% | 2.00 g | 98.3% | | | | | | | | |
| Vinamul 3650 | 52% | | | | | | 3.85 g | 98.0% | 2.00 g | 98.3% | | | | |
| Haloflex 202. Coalescent 2-butoxy-ethanol | 60% | | | | | | | | | | 3.33 g | 97.7% | 2.00 g | 98.3% |
| Lambda-Cyhalothrin* Content | | | 3.4 g | 100.0% | 2.0 g 0.015 g | 100.0% 0.77% | 3.9 g | 100.0% | 2.0 g 0.015 g | 100.0% 0.77% | 3.4 g | 100.0% | 2.0 g 0.015 g | 100.0% 0.77% |
| | | | Batch Size = 2.00 g Ex #14 | | | | Batch Size = 2.00 g Ex #15 | | | | Batch Size = 2.00 g Ex #16 | | | |

TABLE 2-continued

| Micro-encapsulated Pesticide | Solids Content | Lambda* Content | Wet Composition | | Dry Composition | | Wet Composition | | Dry Composition | | Wet Composition | | Dry Composition | |
|---|---|---|---|---|---|---|---|---|---|---|---|---|---|---|
| Aminoplast CS Latexes | 44.36% | 20.00% | 0.08 g | 1.5% | 0.03 g | 1.7% | 0.08 g | 1.7% | 0.03 g | 1.7% | 0.08 g | 1.3% | 0.03 g | 1.7% |
| Vinacryl 40224 | 40% | | 4.91 g | 98.5% | 1.97 g | 98.3% | | | | | | | | |
| Neocryl A-1049 | 40% | | | | | | 3.94 g | 89.4% | 1.58 g | 78.8% | | | | |
| Neopac E106 | 33% | | | | | | | | | | 5.96 g | 98.7% | 1.97 g | 98.3% |
| Coalescent 2-butoxy-ethanol | | | | | | | | | | | | | | |
| | | | 5.0 g | 100.0% | 2.0 g | 100.0% | 4.4 g | 100.0% | 2.0 g | 100.0% | 6.0 g | 100.0% | 2.0 g | 100.0% |
| Lambda-Cyhalothrin* Content | | | | | 0.015 g | 0.77% | | | 0.015 g | 0.77% | | | 0.015 g | 0.77% |
| | | | Batch Size = 2.00 g | | | | Batch Size = 2.00 g | | | | Batch Size = 2.00 g | | | |

TABLE 3

| Micro-encapsulated Pesticide | Solids Content | Lambda* Content | Wet Composition | | Dry Composition | | Wet Composition | | Dry Composition | | Wet Composition | | Dry Composition | |
|---|---|---|---|---|---|---|---|---|---|---|---|---|---|---|
| | | | Ex #17 | | | | Ex #18 | | | | Ex #19 | | | |
| High X-linked Latexes | 31.23% | 9.68% | 0.16 g | 4.7% | 0.05 g | 2.5% | 0.16 g | 4.1% | 0.05 g | 2.5% | 0.16 g | 4.7% | 0.05 g | 2.5% |
| Permax 803 | 60% | | 3.25 g | 95.3% | 1.95 g | 97.5% | | | | | | | | |
| Vinamul 3650 | 52% | | | | | | 3.75 g | 95.9% | 1.95 g | 97.5% | | | | |
| Haloflex 202. | 60% | | | | | | | | | | 3.25 g | 95.3% | 1.95 g | 97.5% |
| Coalescent 2-butoxy-ethanol | | | | | | | | | | | | | | |
| Lambda-Cyhalothrin Content | | | 3.4 g | 100.0% | 2.0 g | 100.0% | 3.9 g | 100.0% | 2.0 g | 100.0% | 3.4 g | 100.0% | 2.0 g | 100.0% |
| | | | | | 0.015 g | 0.77% | | | 0.015 g | 0.77% | | | 0.015 g | 0.77% |
| | | | Batch Size = 2.00 g | | | | Batch Size = 2.00 g | | | | Batch Size = 2.00 g | | | |
| | | | Ex #20 | | | | Ex #21 | | | | Ex #22 | | | |
| High X-linked Latexes | 31.23% | 9.68% | 0.16 g | 3.2% | 0.05 g | 2.5% | 0.16 g | 3.6% | 0.05 g | 2.5% | 0.16 g | 2.6% | 0.05 g | 2.5% |
| Vinacryl 40224 | 40% | | 4.88 g | 96.8% | 1.95 g | 97.5% | | | | | | | | |
| Neocryl A-1049 | 40% | | | | | | 3.90 g | 87.7% | 1.56 g | 78.0% | | | | |
| Neopac E106 | 33% | | | | | | | | | | 5.91 g | 97.4% | 1.95 g | 97.5% |
| Coalescent 2-butoxy-ethanol | | | | | | | | | | | | | | |
| Lambda-Cyhalothrin Content | | | 5.0 g | 100.0% | 2.0 g | 100.0% | 4.4 g | 100.0% | 2.0 g | 100.0% | 6.1 g | 100.0% | 2.0 g | 100.0% |
| | | | | | 0.015 g | 0.77% | | | 0.015 g | 0.77% | | | 0.015 g | 0.77% |
| | | | Batch Size = 2.00 g | | | | Batch Size = 2.00 g | | | | Batch Size = 2.00 g | | | |

TABLE 4

| Micro-encapsulated Pesticide | Solids Content | Pesticide Content | Wet Composition | | Dry Composition | | Wet Composition | | Dry Composition | | Wet Composition | | Dry Composition | |
|---|---|---|---|---|---|---|---|---|---|---|---|---|---|---|
| | | | Ex #23 | | | | Ex #24 | | | | Ex #25 | | | |
| Force 30 CS (tefluthrin) | 55% | 30% | 0.05 g | 1.5% | 0.03 g | 1.4% | 0.05 g | 1.3% | 0.03 g | 1.4% | | | | |
| Gamma Cyhalothrin CS | 10% | 1.50% | | | | | | | | | 1.03 g | 24.5% | 0.10 g | 5.1% |
| Latexes | | | | | | | | | | | | | | |
| Permax 803 | 60% | | 3.29 g | 98.5% | 1.97 g | 98.6% | | | | | 3.16 g | 75.5% | 1.90 g | 94.9% |
| Vinamul 3650 | 52% | | | | | | 3.79 g | 98.7% | 1.97 g | 98.6% | | | | |
| Coalescent 2-butoxy-ethanol | | | | | | | | | | | | | | |
| Pesticide Content | | | 3.3 g | 100.0% | 2.0 g | 100.0% | 3.8 g | 100.0% | 2.0 g | 100.0% | 4.2 g | 100.0% | 2.0 g | 100.0% |
| | | | | | 0.015 g | 0.77% | | | 0.015 g | 0.77% | | | 0.015 g | 0.77% |
| | | | Batch Size = 2.00 g | | | | Batch Size = 2.00 g | | | | Batch Size = 2.00 g | | | |
| | | | Ex #26 | | | | Ex #27 | | | | Ex #28 | | | |
| Force 30 CS | 55% | 30% | | | | | | | | | | | | |
| Gamma Cyhalothrin CS | 10% | 1.50% | 1.03 g | 22.0% | 0.10 g | 5.1% | | | | | | | | |
| Latexes | | | | | | | | | | | | | | |
| Permax 803 | 60% | | 3.65 g | 78.0% | 1.90 g | 94.9% | 3.33 g | 97.7% | 2.00 g | 98.9% | | | | |
| Vinamul 3650 | 52% | | | | | | | | | | 3.80 g | 98.0% | 1.98 g | 98.8% |
| Coalescent 2-butoxy-ethanol | | | | | | | | | | | | | | |
| Pesticide Content | | | 4.7 g | 100.0% | 2.0 g | 100.0% | 3.4 g | 100.0% | 2.0 g | 100.0% | 3.9 g | 100.0% | 2.0 g | 100.0% |
| | | | | | 0.015 g | 0.77% | | | 0.015 g | 0.77% | | | 0.015 g | 0.77% |
| | | | Batch Size = 2.00 g | | | | Batch Size = 2.00 g | | | | Batch Size = 2.00 g | | | |

TABLE 3

| Micro-encapsulated Pesticide | Solids Content | Lambda Content | Wet Composition | | Dry Composition | | Wet Composition | | Dry Composition | | Wet Composition | | Dry Composition | |
|---|---|---|---|---|---|---|---|---|---|---|---|---|---|---|
| | | | Ex #29 | | | | Ex #30 | | | | Ex #31 | | | |
| Scimitar/Demand 10CS Fungicide Millbases | 32.50% | 9.68% | 0.16 g | 4.7% | 0.05 g | 2.6% | 0.16 g | 4.1% | 0.05 g | 2.6% | 0.16 g | 4.7% | 0.05 g | 2.6% |
| Chlorothalonil | 55% | 50% | 0.03 g | 0.9% | 0.02 g | 0.8% | 0.03 g | 0.8% | 0.02 g | 0.8% | | | | |
| Difenoconazole | 55% | 50% | | | | | | | | | 0.03 g | 0.9% | 0.02 g | 0.8% |
| Latexes | | | | | | | | | | | | | | |
| Permax 803 | 60% | | 3.22 g | 94.4% | 1.93 g | 96.6% | | | | | 3.22 g | 94.4% | 1.93 g | 96.6% |
| Vinamul 3650 | 52% | | | | | | 3.71 g | 95.1% | 1.93 g | 96.6% | | | | |
| Coalescent 2-butoxy-ethanol | | | 3.4 g | 100.0% | 2.0 g | 100.0% | 3.9 g | 100.0% | 2.0 g | 100.0% | 3.4 g | 100.0% | 2.0 g | 100.0% |
| Lambda-Cyhalothrin Content | | | | | 0.015 g | 0.77% | | | 0.015 g | 0.77% | | | 0.015 g | 0.77% |
| | | | Batch Size = 2.00 g | | | | Batch Size = 2.00 g | | | | Batch Size = 2.00 g | | | |

TABLE 3-continued

| Micro-encapsulated Pesticide | Solids Content | Lambda Content | Wet Composition | | Dry Composition | | Wet Composition | | Dry Composition | | Wet Composition | | Dry Composition | |
|---|---|---|---|---|---|---|---|---|---|---|---|---|---|---|
| | | | Ex #32 | | | | Ex #33 | | | | Ex #34 | | | |
| Scimitar/Demand 10CS Fungicide Millbases | 32.50% | 9.68% | 0.16 g | 4.1% | 0.05 g | 2.6% | 0.16 g | 4.7% | 0.05 g | 2.6% | 0.16 g | 4.1% | 0.05 g | 2.6% |
| Difenoconazole | 55% | 50% | 0.03 g | 0.8% | 0.02 g | 0.8% | | | | | | | | |
| Azoxystrobin Latexes | 55% | 50% | | | | | 0.03 g | 0.9% | 0.02 g | 0.8% | 0.03 g | 0.8% | 0.02 g | 0.8% |
| Permax 803 | 60% | | | | | | 3.22 g | 94.4% | 1.93 g | 96.6% | | | | |
| Vinamul 3650 | 52% | | 3.71 g | 95.1% | 1.93 g | 96.6% | | | | | 3.71 g | 95.1% | 1.93 g | 96.6% |
| Coalescent 2-butoxyethanol | | | 3.9 g | 100.0% | 2.0 g | 100.0% | 3.4 g | 100.0% | 2.0 g | 100.0% | 3.9 g | 100.0% | 2.0 g | 100.0% |
| Lambda-Cyhalothrin Content | | | | | 0.015 g | 0.77% | | | 0.015 g | 0.77% | | | 0.015 g | 0.77% |
| | | | Batch Size = 2.00 g | | | | Batch Size = 2.00 g | | | | Batch Size = 2.00 g | | | |

Example 35

The composition of example 1 was coated by a laboratory coater onto a polyethylene sheet (approx 50 cm square) substrate and tested in a Forestry Service termite trial. These squares were placed under a cast concrete slab in the centre of which a hole had been left (approx 10 cm square). A suitable sample of wood was place in this hole in contact with the treated plastic sheet. The test was then covered to avoid heavy rainfall on the wooden sample. After 16 months the experimental treatment showed no termite damage, whereas other control treatments had been significantly damaged (indeed showing attack commencing within the first month of the study).

What is claimed is:

1. A coating composition comprising an aqueous dispersion of a pesticidally effective amount of at least one microencapsulated pesticide selected from lambda cyhalothrin, fipronil and thiamethoxam and a film-forming effective amount of at least one latex polymeric film-forming, water-insoluble binder; wherein the composition has a minimum film forming temperature (MFFT) of from 0 to 50 degrees Celsius and a coating prepared from the composition is substantially water-impermeable according to ASTM D 870-2 at 20 degrees Celsius and wherein the coating composition further comprises triclosan.

2. The coating composition according to claim 1, wherein the microcapsule wall comprises a polyurea.

3. The coating composition according to claim 1, wherein the latex polymer comprises a polymer selected from polymers of styrene, alkyl styrenes, isoprene, butadiene, acrylonitrile, lower alkyl acrylates and methacrylates, vinyl chloride, vinylidene chloride, vinyl esters of lower carboxylic acids and alpha, beta-ethylenically unsaturated carboxylic acids and silicone.

4. The coating composition according to claim 1, wherein the binder comprises a polymer dispersion having a particle size from 0.03 to 20 microns.

5. The coating composition according to claim 4, wherein the binder comprises a polymer dispersion having a particle size is from 0.1 to 10 microns.

6. The coating composition according to claim 1, wherein the binder is present in the coating composition in an amount sufficient to provide a cured coating which comprises at least about 50% by weight of the binder.

7. The coating composition according to claim 1, which further comprises at least one multi-functional monomer.

8. The coating composition according to claim 7, which further comprises at least one bi-functional monomer.

9. The coating composition according to claim 1, further comprising at least one additive selected from non-encapsulated pesticides, rheology control agents, thickeners, surfactants, pigments, fillers, dispersants, freeze-thaw stabilizers and coalescents.

10. A coating composition according to claim 9, wherein the filler is selected from clay, calcium carbonate, glass fiber and titanium dioxide.

* * * * *